United States Patent [19]

Vannice et al.

[11] 4,093,643

[45] June 6, 1978

[54] CATALYTIC FORMATION OF HYDROCARBONS FROM CO, $H_2$ MIXTURES AND PROCESS FOR MAINTAINING CATALYTIC ACTIVITY

[75] Inventors: M. Albert Vannice, Boalsburg, Pa.; Robert L. Garten, Summit, N.J.

[73] Assignee: Exxon Research and Engineering Company, Linden, N.J.

[21] Appl. No.: 769,574

[22] Filed: Feb. 17, 1977

Related U.S. Application Data

[63] Continuation-in-part of Ser. No. 644,561, Dec. 24, 1975, abandoned.

[51] Int. Cl.² .............................................. C07C 1/04
[52] U.S. Cl. ......................... 260/449 M; 260/449 R; 252/455 Z; 252/460; 252/466 R
[58] Field of Search ........................ 260/449 M, 449 R

[56] References Cited

U.S. PATENT DOCUMENTS

| | | | |
|---|---|---|---|
| 3,625,664 | 12/1971 | Padovani | 260/449 M |
| 3,854,895 | 12/1974 | Muller | 260/449 M X |

OTHER PUBLICATIONS

Shultz et al., Bur. of Mines, Report of Investigations, No. 6974 pp. 1-11, 1967.
Collier, Catalysis in Practice, Reinhold Publishing, New York, 1957, pp. 14-15.
Vannice I, J. of Catalysis 37, 449-461 (1975).
Aben, J. of Catalysis 10, 224, 229 (1968).
Vannice II, J. of Catalysis 40, 192-134, 1975.

*Primary Examiner*—Howard T. Mars
*Attorney, Agent, or Firm*—Joseph J. Allocca

[57] ABSTRACT

A method for producing low molecular weight organic compounds, said method comprising the step of passing a mixture of CO and $H_2$ over palladium supported on a suitable acidic metal oxide at a temperature and pressure sufficient to form said organic compounds. The palladium is highly dispersed on the chosen support and has a crystallite size of less than 100 A, preferably less than 70 A, most preferably, less than 40 A. In this state, the surface Pd atoms have a much higher activity than surface Pd atoms of very large Pd crystallites. To insure maintenance of such high activity and small crystallite size for a substantial period during the course of the reaction, the synthesis reactions are run at reactor bed temperatures below which agglomeration of crystallites is avoided, i.e., at temperatures below 350° C., preferably about 325° C., most preferably 300° C.

9 Claims, 1 Drawing Figure

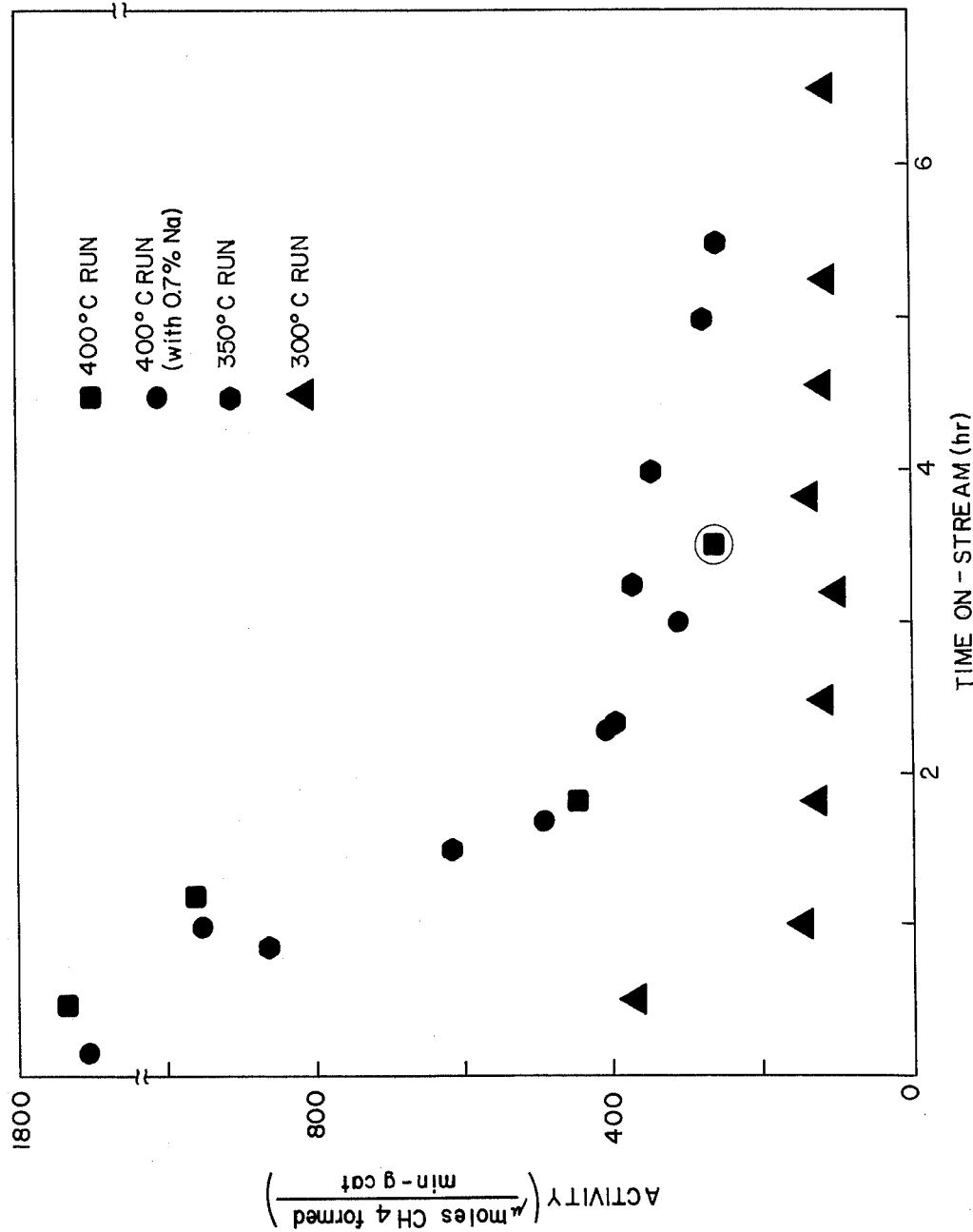

CATALYTIC FORMATION OF HYDROCARBONS FROM CO, H$_2$ MIXTURES AND PROCESS FOR MAINTAINING CATALYTIC ACTIVITY

CROSS REFERENCE TO RELATED APPLICATIONS

This application is a continuation-in-part of Ser. No. 644,561 filed Dec. 24, 1975 now abandoned, which is a Refile of Ser. No. 523,407 filed Nov. 13, 1974 (now abandoned) which was a Refile of Ser. No. 491,221 filed on July 24, 1974 (now abandoned).

BACKGROUND OF THE INVENTION

This invention pertains to improvements in the production of organic compounds from carbon monoxide and hydrogen. In one aspect, the invention relates to passing a feedstream containing hydrogen and carbon monoxide over a supported palladium catalyst in which palladium is highly dispersed and of small crystallite size, i.e. less than 100 A, preferably less than 70 A, most preferably less than 40 A and to a process for maintaining the palladium in the dispersed state.

In still another aspect, the invention is concerned with improvements in the production of methane from a feedstream containing H$_2$ and CO.

Although a vast amount of research and development has been conducted over the past 50 years pertaining to the Fischer-Tropsch synthesis (the reaction between CO and H$_2$ to form organic compounds) almost no effort has been made to study the capability of noble metals to catalyze this reaction.

Although the metals of the palladium group are all generally active as hydrogenation-dehydrogenation catalysts, they differ considerably in their ability to catalyze the various reactions between carbon monoxide and hydrogen. Ruthenium has been known for many years to be an effective catalyst in the Fischer-Tropsch synthesis and in the catalytic synthesis of methane from carbon monoxide and hydrogen, the reaction producing high molecular weight waxes at high pressures and large quantities of methane at atmospheric pressure. Suspensions of ruthenium oxides in a hydrocarbon solvent have been shown to possess exceptionally high activity, the CO—H$_2$ reaction being measurable at 100° C. By contrast, the other unsupported platinoid metals are much inferior catalysts for these reactions. Unsupported metals such as rhodium and osmium have been shown to exhibit some activity at elevated temperatures whereas palladium and platinum are generally inert for both the Fischer-Tropsch synthesis and the methanation reaction under these same conditions.

Of the nine Group VIII metals of interest, iron, cobalt and nickel have been extensively studied and large quantities of information exist in the literature. All three produce significant amounts of methane from a CO + H$_2$ feedstream but nickel is the most selective toward methane and is presently the commercially used catalyst for the methanation reaction.

In an article authored by F. Fischer, H. Tropsch and P. Dilthey, Brennstoff-Chemie 6, 265 (1925), the methanation activities of a series of unsupported metals were studied to determine the order of their activity. The metals in order of decreasing activity were ruthenium, iridium, rhodium, nickel, cobalt, osmium, platinum, iron, molybdenum, palladium and silver. However, none of these activities was corrected for differences in metal surface areas. Surface area variations for the different metals could significantly alter the order of activities of the metals. Palladium was found to be the least active Group VIII metal giving no conversion at 300° C and negligible conversion at 400° C.

In another article by H. Pichler, Adv. in Catalysis, IV, 271 (1952), ruthenium was described as the most active catalyst for the low temperature, high pressure synthesis of high molecular weight materials. It was verbally stated that ruthenium and osmium gave appreciable amounts of liquid and solid products, platinum was "much less suitable" as a catalyst for this reaction, and palladium and iridium gave only traces of products.

In another article by McKee, D. W., J. Catal. 8 240 (1967), the interaction of CO + H$_2$ at 1 atmosphere over various unsupported Group VIII metals was studied by the author. He found that Pd was completely inactive toward methane formation whereas rhodium and iridium produced small amounts of methane at 200° C. and ruthenium was quite active at 100° C.

U.S. Bureau of Mines Report #6974 (1967) discloses the only data concerning Pd placed on a metal oxide support (Pd/Al$_2$O$_3$). Contrary to the findings of the present application, the Bureau of Mines found that a Pd/Al$_2$O$_3$ catalyst was the least active of the noble metals.

However, no information is disclosed in this Report as to their pretreatment procedure of the catalyst. We have discovered that a careful pretreatment procedure of the catalyst is required for insuring that Pd/Al$_2$O$_3$ possesses high activity as a catalyst in the methanation reaction and that such high activity can be maintained by running the process within certain operating parameters.

U.S. Pat. No. 3,625,664 to Padovani, teaches a process for the production of rich fuel to replace natural gas by means of catalytic hydrogasification under pressure of fluid hydrocarbons. This patent discloses that catalyst systems such as nickel, ruthenium, iron, cobalt, palladium, or platinum on a support such as alumina, and/or magnesia and/or silicon oxides and/or calcium oxides may be used to generate methane from CO and H$_2$. This patent is not specifically directed to Pd on Al$_2$O$_3$ or other acidic supports as is the instant invention and does not recognize or teach the criticality of the palladium being well dispersed and of small crystallite size on the support. Nor does the patent teach the necessity of the support being acidic or the temperature sensitivity of the system. Finally, the patent while broadly disclosing a supported palladium catalyst did not actually utilize such a catalyst, all working examples being Co, Ni, Mo catalysts and iron-zinc oxide catalysts.

Therefore, the understanding of the prior art was that palladium was not a particularly good catalyst for the production of methane from CO and H$_2$. All of these authors who actually conducted experiments studied palladium in its unsupported state and employed it in its powder form, except for the U.S. Bureau of Mines, while U.S. Pat. No. 3,625,664 did not test palladium at all.

The present invention has found that if palladium is supported on various acidic metal oxide supports in a highly dispersed state, it has an especially high specific activity to catalytically produce low molecular weight organic compounds, especially methane, from a mixture of CO and hydrogen. This enhanced activity is 60-70 times greater than any enhancement due only to an increase in Pd metal surface area due to increased dispersion. Supported palladium catalysts have several advantages over commercial nickel catalysts which include (1) better activity maintenance, (2) better tolerance to sulfur, (3) better selectivity to methane and (4) more tolerance to higher CO pressures and lower temperatures as palladium does not form volatile metal carbonyl as nickel would do under similar conditions.

Briefly, the subject invention relates to a method for producing low molecular weight organic compounds, primarily methane, said method comprising the step of passing a mixture of CO and $H_2$ over palladium supported on a suitable acidic metal oxide at a reactor bed temperature below which agglomeration of the crystallites is avoided for a reasonable period (i.e. for enough time to make operation of the catalyst economically feasible) at a temperature of between 100°–400° C., preferably 300°–350° C., more preferably at 300–325, most preferably at 300° C., and pressure sufficient to form said organic compounds.

The instant invention teaches a process for maintaining the activity of a catalyst selected from the group consisting of palladium on alumina and palladium on hydrogen-y-zeolite used to produce low molecular weight organic compounds comprising substantially methane, said process consisting of the steps of passing a mixture of CO and $H_2$ over palladium supported on an acidic metal oxide selected from the group consisting of alumina and hydrogen-y-zeolite wherein the catalytic activity is maintained by maintaining the palladium metal particle size at less than 100 A which is accomplished by running at a reactor bed temperature of between 100° and 400° C at a pressure ranging from 1 to 500 atmospheres and at a GHSV of from 1200–4600 $hr^{-1}$. In the practice of the invention the $H_2/CO$ ratio may range from 1 to 5 and the amount of palladium may range from 0.2 to 2.0 wt. % based on the total weight of the support plus the palladium. Preferably, the temperature of the reactor bed ranges from 300° to 400° C.

The catalyst used in accordance with this invention is formed by the steps of impregnating a suitable support material with a salt solution of the palladium followed by heat treating the impregnated support to form a chemical complex at the surface of the support and to drive off moisture. The complex is highly dispersed and the palladium has a crystallite size of less than 100 A, preferably less than 70 A, most preferably less than 40 A.

Palladium may be added to the catalyst in the form of a solution containing a soluble palladium salt or any other palladium salt which is soluble in the solvent used for the impregnation.

The impregnated support in powder or granular form is then treated by establishing time-temperature relationships suitable to produce a chemical change on the surface of the support and to remove water and adsorbed oxygen. Suitably, the impregnated support can be heated in air, in an inert atmosphere or in vacuum, e.g. 20–29 inches of mercury, and from about 150° to about 650° C., preferably from about 200° to about 430° C. for periods ranging from about 0.5 to about 4 hours, or preferably from about 1 to about 2 hours. On the other hand, the reaction between the salt and support can be accomplished by the elevated temperatures while moisture is stripped from the support with nitrogen or other nonreactive gases. If desirable, the impregnation and heat treating steps can be conducted in multiple stages, for example, the support can be impregnated and then dried, or partially dried at low temperature. Support can then be reimpregnated and again dried or partially dried. The heat treatment per se can also be conducted in multiple stages, if desired. The impregnated support, to facilitate handling, can thus be subjected to a first rather mild heat treatment to dry the support and thence in a second step, to a more severe treatment to produce the desired chemical change at the surface. This pretreatment procedure is employed to obtain small Pd crystallites and is similar to that employed by Aben and disclosed in the *Journal of Catalysts* 10, 224 (1968). The Pd metal dispersions of the instant invention are such that the Pd particle size is <100A, preferably less than 70 A, most preferably less than 40 A.

Suitable supports are the oxides in Groups IIIA and IVA, V-B and VI-B of the Periodic Chart of the Elements and are described in a Table found in the *Handbook of Chemistry and Physics*, Chemical Rubber Company, 45th ed., (1964) page B-2. Acidic metal oxides, particularly alumina, are essential to obtain maximum activity enhancement. Alumina supports in fact, are quite outstanding from a cost effect standpoint and are readily available. Silica-free alumina has been found especially suitable though silica-alumina is also highly active. Silica-alumina, i.e., acidic zeolites, certain natural acidic clays, diatomaceous earth, e.g., kieselguhr and other supports are also useful. Silicon dioxide, and mixtures of silicon dioxide and aluminum oxide are also used in this invention as well as the acidic zeolites. In fact, any acidic refractory oxide that will give well-dispersed palladium is suitable in the use of this invention, with alumina, silica-alumina (for example, acidic zeolites) being preferred.

Methane formation is the predominant reaction desired in the subject invention and the catalyst incorporates an acidic support, i.e. palladium-$Al_2O_3$. The palladium loading ranges from 0.01 to 5 wt. % based on the total weight of the support + palladium and the preferred amount of palladium ranges from 0.2 to 2 wt. % based upon the total weight of the support + palladium. In the methane formation, the hydrogen to CO mole ratio ranges from 0.5 to 15 and is preferred from 1 to 5. The pressure ranges from 1 to 500 atmospheres and is preferred from 1 to 20 atmospheres; temperature of the reaction bed ranges from 100° to 400° C., preferably 300–350, more preferably 300°–325° C., most preferably about 300° C.

Reaction bed temperatures of less than 350° C. are necessary for the maintenance of catalytic activity during the course of the process, i.e. for a long enough time to make operation of the catalyst economically feasible. Exposure to reactor bed temperatures in excess of 350° C. results in marked decreases in surface area (i.e. agglomeration of the palladium, evidenced by crystallite sizes greater than 100 A) which result in decreased activity. Highly dispersed Pd/$Al_2O_3$ catalysts possess very high initial activity at 400° C. with over 70% of the CO converted. These conversions are much higher than those obtained by the U.S. Bureau of Mines even though the temperature is 100° C. lower and the space velocity is 14 times higher. However, at these high conversions and high temperatures, the catalysts deactivate rapidly and possess only about 1/10 their activity after 3½ hours on-stream. As shown in Table I, a concomitant loss in metal surface area occurs and accounts for much of the loss in activity. At 350° C. the catalyst still shows an activity decline although it is not so marked. The greater metal surface area is sufficient to give this catalyst a higher activity after 3 hours on-stream than the catalyst run at 400° C. even though the temperature is 50° C. lower. Finally, when run at 300° C., the catalyst shows some activity decrease during the first hour but then stabilizes and retains a constant activity during the remainder of the test run. This demonstrates a necessary limitation in reactor bed temperatures such that at 300° C. the catalyst is very active and stable, possessing at this temperature 50% the activity of the catalyst run at 400° C., whereas at 350° C. the activity continuously declines and at 400° C. the activity declines very precipitously. The preferred temperature range is therefore 300°-350° C., with 325° C. the more preferred temperature, and 300° C. the most preferred temperature.

This behavior is more clearly evidenced in FIG. 1. The two catalyst samples run at 400° C. have much higher initial rates, as expected due to the higher temperature, but a rapid decline occurs with increasing time on-stream. A less rapid decline occurs at 350° C. while very stable activity maintenance exists at 300° C. Therefore, between 300° and 350° C. the $Pd/Al_2O_3$ catalyst can be utilized without deactivation. This figure not only shows a temperature window in which both high activity and activity maintenance can be obtained together, but also provides a clear explanation of the Bureau of Mines result. At their temperature of 500° C., an even more rapid and severe activity decline is expected to occur creating a catalyst with very low activity. The exceedingly low activity is shown in Table II by calculating an activity from the Bureau of Mines data. Even at 500° C. the activity per gram catalyst is lower than the high-activity $Pd/Al_2O_3$ catalyst disclosed here. Since the activation energy for this reaction has been found to be $-19,700$ cal/mole over $Pd/Al_2O_3$, the rate at 300° C. can be calculated. If this is done and correction is also made for space velocity differences, the activity for the Bureau of Mines catalyst is only 0.044, more than 1000 times lower than the catalyst of the present invention. This result is also shown in Table II.

The data in Table I shows very clearly that increasing the reactor temperature decreases the available Pd surface area as indicated by the ratio of adsorbed CO to the total number of Pd atoms in the catalyst. The catalysts subjected to the highest temperatures show an order of magnitude drop in metal surface area while the decrease in the sample heated only to 300° C is much less severe and still allows the catalyst to possess a very high activity.

One catalyst sample had 0.7 wt. % Na added to establish the effect of this component. Sodium clearly has a detrimental effect as it blocks part of the Pd surface to CO adsorption as shown in Table I by the CO uptake on the fresh reduced sample. A concomitant decrease in initial activity occurs as shown in FIG. 1. However, after several hours on-stream, both the final activities and CO uptakes are identical indicating that the Na has been removed from the Pd surface, possibly by a washing effect since large quantities of water are produced in the course of the reaction.

Table II demonstrates that these catalysts achieve significant conversions although the temperatures are 100°–200° C lower than the Bureau of Mines runs and the space velocities are 4 to 21 times higher.

TABLE I

| | Chemisorption Data for Used 0.5% $Pd/Al_2O_3$ Catalysts | | | |
|---|---|---|---|---|
| Run | Reaction Temp. (° C) | CO Uptake (μmole/g) | CO/Pd | Pd Crystallite Size (avg.) (A) |
| 1a | Fresh | 46.5 | 0.99 | <15 |
| 1b | 400 | 3.8 | 0.081 | 130 |
| 2a w/0.7% Na added | Fresh | 16.5 | 0.35 | — |
| 2b w/0.7% Na added | 400 | 3.8 | 0.081 | 130 |
| 3 | 350 | 7.5 | 0.16 | 70 |
| 4 | 300 | 11.6 | 0.25 | 40 |

TABLE II

| | Kinetic Data for CO Conversion | | | | | |
|---|---|---|---|---|---|---|
| Run | Temp. (° C) | Pressure (ATM) | GHSV ($hr^{-1}$) | On-Stream (hr) | CO Conversion to $CH_4$ (%) | Catalyst Activity (μ mole $CH_4$/min · g cat) |
| 2 | 408 | 20.3 | 4500 | ½ | 71 | 1740 |
| | 406 | 20.7 | 5300 | 3½ | 18 | 258 |
| 3 | 402 | 20.7 | 3200 | 1 | 43 | 950 |
| | 399 | 20.9 | 1200 | 3½ | 30 | 262 |
| 4 | 352 | 21.1 | 6800 | ¾ | 17 | 866 |
| | 351 | 21.6 | 6900 | 5½ | 5.0 | 259 |
| 5 | 301 | 21.0 | 3000 | ½ | 25 | 363 |
| | 298 | 20.7 | 4500 | 1 | 4.3 | 142 |
| | 304 | 20.7 | 4600 | 6¼ | 3.4 | 117 |
| Bureau of Mines | 499 | 21 | 318 | — | 35.5[a] | 56 (est.) |
| " | 300 | 21 | 4600 | — | — | 0.004 (calc.) |

[a]$[H_2+CO]$ conversion to all hydrocarbon products.

The methanation reaction occurs very selectively over Pd and only very small amounts of other hydrocarbons are detected. In fact, it is surprising to note that Pd is the most selective methanation catalyst of the Group VIII metals. A portion of this invention is the discovery that the specific activity (rate per unit surface area of metal) of Pd can be enhanced by placing the metal on particular supports, especially $Al_2O_3$, and pretreating this catalyst properly to maintain small Pd crystallites. Other supports will also enhance activity, but the greatest enhancements come from acidic supports, as indicated in Table III. The highest activity is achieved with Pd supported on the more acidic metal oxides, such as $Al_2O_3$, and the smallest improvement in activity occurs when the least acidic support, $SiO_2$ is used. That the rate per surface Pd atom is greatly increased is clear from a comparison of rates in column 4. The specific activity of $Pd/Al_2O_3$ is 70 times greater than the rate of unsupported Pd.

The specific activity of a catalyst is represented by a "Turnover Number", defined as the number of CO molecules reacted per second per site on the metal surface. The number of sites is determined by selective chemisorption techniques using a gas such as carbon monoxide or hydrogen. Such gases are selectively chemisorbed on the metal surface and by employing justified, common assumptions such as 1 hydrogen atom adsorbs on every surface metal atom or 1 CO molecule adsorbs on every surface metal atom, the number of surface metal atoms, $M_s$, can be calculated. This value then represents the total number of metal surface sites and can also be used to calculate the metal dispersion, $D$, defined by $D = M_s/M_t$ where $M_t$ is the total number of metal atoms in the sample.

Such a representation of catalyst activity is very meaningful since it allows direct comparisons not only between different metals but also between different metal loadings of the same metal catalyst. Space velocity measurements do not correct for different metal loadings in different catalysts, or any differences in metal surface areas at the same loading, i.e. dispersion effects. A comparison of turnover numbers, therefore, already has normalized out differences in surface area due to dispersion effects. If conversion data is desired, it is easily calculated from the following formula which assumes no diffusional limitations:

$$\text{Conversion} = (\text{Turnover Number} \frac{\text{molecules}}{\text{site-sec}})(M_s)$$

$$(\text{Reactant gas flow} \frac{\text{ccSTP}}{\text{sec}})(\frac{44.6 \ \mu\text{mole gas}}{1 \text{ cc gas}})(\frac{6.02 \times 10^{17} \text{ molecules}}{\mu \text{ mole}})$$

These supported palladium catalysts heretofore unrecognized as an active selective catalyst in the reaction between CO and hydrogen are useful in any process producing such a mixture such as gasification of coal, residuum, oil shale, tar sands, etc. All these processes can utilize these catalysts to produce methane.

In order to describe the workings of the invention, the inventive process is described in the following illustrative examples.

EXAMPLE 1

Methods of Catalyst Preparation

A. 2% Palladium on aluminum oxide

Ten and one-half milliliters of a solution of $PdCl_2$ containing 0.3563g of palladium was added to 17.82 g of aluminum oxide. The aluminum oxide had a surface area of ~ 180 m²/g. The mixture was then stirred well to facilitate uniform contacting of the components and then dried for 16 hrs. at 120° C and calcined in air for 4 hrs. at 500° C.

B. 4.75% Palladium on silica ($SiO_2$)

Forty-four milliliters of a solution containing 0.9974g of palladium was added to 20g of Cab-o-sil ($SiO_2$). The surface area of the Cab-o-sil was ~300 M²/g. The Cab-o-sil and palladium solution were thoroughly mixed and the resulting catalyst was dried for 16 hrs. at 120° C in air.

C. 0.5% Palladium on Hydrogen-Y Zeolite

This material was a commercial catalyst preparation.

D. 0.5% Pd/$\eta$-$Al_2O_3$

Twenty grams of $\eta$-$Al_2O_3$ was weighed into a beaker. Twenty-six cc of distilled water was added to 1.03 cc of a $PdCl_2$ solution containing 0.098 g Pd/cc. This mixture was added to the $\eta$-$Al_2O_3$ to form a slurry which was stirred overnight to allow adsorption of the palladium onto the $\eta$-$Al_2O_3$. The liquid was removed by filtration. The catalyst was then dried at 120° C in air for 16 hours and at 260° C in air for 4 hours.

E. 0.5% Pd, 0.7% Na/$\eta$-$Al_2O_3$

Fifteen grams of $\eta$-$Al_2O_3$ was weighed into a beaker. 0.685 cc of 1N NaOH solution was diluted with 6.82 cc distilled water and this mixture was added to the $\eta$-$Al_2O_3$ while thoroughly stirring the $\eta$-$Al_2O_3$ with a spatula. The sample was then dried for 16 hours at 120° C in air and calcined in air for 4 hours at 600° C.

Seven grams of the 0.7% Na/$\eta$-$Al_2O_3$ was weighed into a beaker. To this was added 0.358 cc of $PdCl_2$ solution containing 0.098 g Pd/cc diluted with 50 cc of distilled water. The mixture was stirred for 16 hours to allow adsorption of the palladium by the support. The liquid was removed by filtration. The catalyst was then dried 16 hours in air at 120° C and 4 hours in air at 260° C.

TABLE III

Enhancement of Methanation Reaction Over Pd Catalysts (1 ATM)

| Catalyst | T (° C) | Hydrocarbon Formation (% CO Conv) | Specific Activity Turnover # (CH₄ Mol. Formed) Pd site.sec | Rate (μmole CH₄) sec · g Pd | CO₂ Formation (%CO Conv) | Hydrocarbon Prod. Analysis, Mole % | | | H₂:CO Ratio | Run # | (Dispersion %) |
|---|---|---|---|---|---|---|---|---|---|---|---|
| | | | | | | C₁ | C₂=C₂ | C₃₊ | | | |
| 2% Pd/Al₂O₃ | 275 | 3.5 | 0.012 | 12.5 | 0.25 | 99 | — 1 — | | 3.0 | 1 | 22 |
| 0.5% Pd/H-Y Zeolite | 275 | 0.6 | 0.0049 | 7.8 | 0.04 | 98 | — 2 — | | 3.0 | 2 | 34 |
| 4.75% Pd/SiO₂ | 275 | 0.3 | 0.00035 | 0.62 | 0.01 | 100 | — — — | | 3.0 | 3 | 38 |
| Pd Black | 275* | — | 0.00017* | 0.0041 | — | 100 | — — — | | 3.0 | 4 | 0.5 |
| 4.75% Pd/SiO₂ | 344 | 1.2 | 0.0041 | 7.3 | 0.06 | 100 | — — — | | 3.0 | 5 | 23 |
| Pd Black | 344 | 1.0 | 0.0023 | 0.055 | 0.94 | 100 | — — — | | 3.0 | 6 | 0.5 |
| 5% Ni/Al₂O₃ | 275 | 55 | 0.032 | — | 2.0 | 95 | — 4 1 | | 3.0 | 7 | 13 |

*Calc. from rate at 344° C and $E_a$ = 25,3000 cal/mole for Pd black.

EXAMPLE 2

The runs described in Table III were made to demonstrate that unsupported palladium in the form of palladium black is indeed quite inactive, the calculated rate at 275° C being extremely low, as shown by Run 6.

Table III clearly shows that supported Pd is much more active than unsupported Pd. When Pd is supported on an acidic support like $Al_2O_3$ (Run 1) the specific activity, expressed as a Turnover Number, is over 70 times more active than unsupported Pd. In all cases of supported Pd, except for three of the 0.5% Pd/Al₂O₃ samples, the metal dispersions were comparable, varying between 20 and 40%. It is, therefore, claimed that the appropriate choice of metal oxide support can greatly enhance the specific activity of the dispersed Pd metal and hence the total activity of the supported Pd catalyst. The more acidic supports, especially $Al_2O_3$, produce the highest activity and the least acidic support, $SiO_2$, gives the least activity enhancement. In all cases, however, supported Pd catalysts have greater activities than unsupported Pd. This is clearly shown by comparing the activities per g Pd listed in column 5, Table III. On this basis, activity is increased more than 1000 times.

Placing Pd on the surface of the appropriate support enhances the specific rate to such an extent that it approaches that of Ni, which is the state-of-the-art methanation catalyst. The data for Ni are shown by Run 7, Table III, for comparison. There is less than a factor of three difference between the specific activity of Pd and that of Ni. Such activity from Pd would not be expected from old work as cited earlier. It is also clear that Pd is a more selective methanation catalyst than Ni, producing only very small amounts of higher molecular weight hydrocarbons.

Although one example of Pd supported on $Al_2O_3$ has been reported (U.S. Bureau of Mines), no rate enhancement due to the support was reported. The pretreatment of this catalyst was not given and Pd metal surface area was not measured thereby eliminating the possibility of comparison with the catalysts disclosed here. However, the results reported by the Bureau of Mine Workers were very discouraging in that they reported $Pd/Al_2O_3$ catalysts as having activity "so low that improvement seems unlikely" and these catalysts did not seem worthy of consideration for commercial use. As we have discussed earlier, the low activity of this catalyst is undoubtedly due to the high temperature utilized with a resulting loss of Pd surface area and activity.

What is claimed is:

1. A process to produce low molecular weight organic compounds comprising substantially methane, said process consisting of the steps of passing a mixture of CO and $H_2$ over palladium supported on an acidic metal oxide selected from the group consisting of alumina and hydrogen-y-zeolite wherein the palladium metal particle size is maintained at less than 100 A by running at a reactor bed temperature of less than 350° C, at a pressure ranging from 1 to 500 atmospheres and at a GHSV of from 1200–4600 $hr^{-1}$.

2. The process according to claim 1 wherein the palladium loading ranges from about 0.01 to 5 wt. % based on the total weight of support and palladium.

3. The process according to claim 1 wherein the palladium loading ranges from about 0.2 to 2 wt. % based on the total weight of support and palladium.

4. The process according to claim 1 further characterized in that the $H_2$ to CO mole ratio ranges from 0.5 to 15.

5. The process according to claim 1 further characterized in that the $H_2$ to CO mole ratio ranges from 1 to 5.

6. The process according to claim 1 wherein the pressure ranges from 1 to 20 atmospheres.

7. The process according to claim 1 wherein the temperature ranges from 300° to 350° C.

8. The process according to claim 1 wherein the temperature is about 300° C.

9. The process according to claim 1 wherein the catalyst selected from the group consisting of palladium on alumina and palladium on hydrogen-y-zeolite is subjected, prior to use, to a temperature of from 150° to 650° C in air or any inert gas for a period of from 0.5 to 4.0 hours.

* * * * *